United States Patent
Lin (10) Patent No.: US 12,153,045 B2
(45) Date of Patent: Nov. 26, 2024

(54) MID-INFRARED INTEGRATED PHOTONICS FOR BIOLOGICAL SENSING

(71) Applicant: The Texas A&M University System, College Station, TX (US)

(72) Inventor: Pao Tai Lin, College Station, TX (US)

(73) Assignee: The Texas A&M University System, College Station, TX (US)

( * ) Notice: Subject to any disclaimer, the term of this patent is extended or adjusted under 35 U.S.C. 154(b) by 823 days.

(21) Appl. No.: 17/324,851

(22) Filed: May 19, 2021

(65) Prior Publication Data

US 2021/0364510 A1    Nov. 25, 2021

Related U.S. Application Data (60) Provisional application No. 63/027,095, filed on May 19, 2020.

(51) Int. Cl.
*G01N 33/543* (2006.01)
*G01N 33/569* (2006.01)
*G02B 6/10* (2006.01)

(52) U.S. Cl.
CPC . *G01N 33/54373* (2013.01); *G01N 33/56983* (2013.01); *G02B 6/102* (2013.01); *G01N 2333/165* (2013.01)

(58) Field of Classification Search
CPC ....... G01N 2333/165; G01N 33/54373; G01N 33/569; G01N 33/56983; G02B 2006/12138; G02B 6/102; G02B 6/12004; G02B 6/12019; G02B 6/12033; G02B 6/122

See application file for complete search history.

(56) References Cited

U.S. PATENT DOCUMENTS

| | | | |
|---|---|---|---|
| 7,559,594 B2 | 7/2009 | Mcmillen | |
| 7,724,997 B2 | 5/2010 | Kittaka et al. | |
| 9,709,504 B2 | 7/2017 | Osterlund et al. | |
| 10,591,410 B2 | 3/2020 | Lin | |
| 10,725,239 B2 | 7/2020 | Lin | |
| 2004/0191765 A1* | 9/2004 | Mozdy ............. | G01N 33/54373 435/5 |

(Continued)

FOREIGN PATENT DOCUMENTS

| WO | WO-2014052502 A1 | 4/2014 |
|---|---|---|
| WO | WO-2014190331 A2 | 11/2014 |

(Continued)

OTHER PUBLICATIONS

"U.S. Appl. No. 16/179,502, Non Final Office Action mailed Aug. 7, 2019", 11 pgs.

(Continued)

*Primary Examiner* — Jennifer Wecker
(74) *Attorney, Agent, or Firm* — Schwegman, Lundberg & Woessner, P.A.

(57) ABSTRACT

A photonic biosensor including a biological probe disposed on a mid-infrared-transparent waveguide can be used to detect biological analytes in biological samples, using specific binding of the analyte to the probe in conjunction with absorption spectroscopy. In various embodiments, the biosensor is used for molecular diagnostics, e.g., to detect oligonucleotides or proteins associated with a coronavirus.

23 Claims, 11 Drawing Sheets

(56) References Cited

U.S. PATENT DOCUMENTS

| | | | |
|---|---|---|---|
| 2006/0228064 A1 | 10/2006 | Hunt et al. | |
| 2009/0041405 A1 | 2/2009 | Dai et al. | |
| 2011/0090484 A1 | 4/2011 | Oesterlund et al. | |
| 2012/0044489 A1* | 2/2012 | Chakravarty | B82Y 20/00 385/12 |
| 2013/0102090 A1* | 4/2013 | Lear | G01N 33/54373 436/501 |
| 2013/0142477 A1 | 6/2013 | Diemeer | |
| 2014/0185042 A1 | 7/2014 | Baets et al. | |
| 2014/0256057 A1* | 9/2014 | Ozawa | G01N 21/6428 422/69 |
| 2016/0139335 A1 | 5/2016 | Abel et al. | |
| 2017/0055906 A1 | 3/2017 | Bremer | |
| 2017/0082544 A1 | 3/2017 | Van Dorpe et al. | |
| 2017/0285264 A1 | 10/2017 | Cote et al. | |
| 2018/0024072 A1* | 1/2018 | Han | G01N 21/7746 435/7.1 |
| 2019/0128798 A1 | 5/2019 | Lin | |
| 2019/0129094 A1 | 5/2019 | Lin | |
| 2019/0361015 A1* | 11/2019 | Mendes | G01N 33/56983 |
| 2021/0364442 A1 | 11/2021 | Lin | |

FOREIGN PATENT DOCUMENTS

| | | |
|---|---|---|
| WO | WO-2018143797 A1 | 8/2018 |
| WO | WO-2020084466 A1 | 4/2020 |

OTHER PUBLICATIONS

"U.S. Appl. No. 16/179,470, Non Final Office Action mailed Sep. 18, 2019", 11 pgs.

"U.S. Appl. No. 16/179,502, Response Filed Nov. 6, 2019 to Non-Final Office Action Mailed Aug. 7, 2019", 9 pgs.

"U.S. Appl. No. 16/179,502, Examiner Interview Summary mailed Nov. 14, 2019", 3 pgs.

"U.S. Appl. No. 16/179,502, Notice of Allowance mailed Nov. 27, 2019", 8 pgs.

"U.S. Appl. No. 16/179,470, Examiner Interview Summary mailed Dec. 18, 2019", 4 pgs.

"U.S. Appl. No. 16/179,470, Response filed Jan. 21, 2020 to Non Final Office Action mailed Sep. 18, 2019", 8 pgs.

"U.S. Appl. No. 16/179,470, Notice of Allowance mailed Mar. 17, 2020", 8 pgs.

Chen, Li, "12.5 pm V hybrid silicon and lithium niobate optical microring resonator with integrated electrodes", Optics Express 27003, vol. 21, No. 22, (Nov. 2013), 8 pgs.

Jin, Tiening, "Monolithically Integrated Si-on-AlN Mid-Infrared Photonic Chips for Real-Time and Label-Free Chemical Sensing", ACS Appl. Mater. Interfaces, vol. 9, (2017), 42905-42911.

Jin, Tiening, "Flexible Mid-infrared Aluminium Nitride Waveguides for Real-time and Label-Free Chemical Sensing", SeTu1E.3. Advanced Photonics Congress (IPR, Networks, NOMA, PS, Sensors, SPPCom) OSA, (2017).

Jin, Tiening, "Monolithic Mid-Infrared Integrated Photonics Using Silicon-on-Epitaxial Barium Titanate Thin Films", ACS Appl. Mater. Interfaces, (2017), 21848-21855.

Jin, Tiening, "Real-Time and Label-Free Chemical Sensor-on-a-chip using Monolithic Si-on-BaTiO3 Mid-Infrared waveguides", Scientific Reports 7, (2017), 8 pgs.

Lin, Pao, "Real-time and label-free chemical sensing using flexible mid-infrared photonic circuits (Conference Presentation)", Proc. SPIE 10662, Smart Biomedical and Physiological Sensor Technology XV, 106620N, (May 2018), 5 pgs.

Lin, Pao, "Label-Free Glucose Sensing Using Chip-Scale Mid-Infrared Integrated Photonics", Adv. Optical Mater, (2016), 1755-1759.

Lin, Pao Tai, "Mid-Infrared Spectrometer Using Opto-Nano?uidic Slot-Waveguide for Label-Free On-Chip Chemical Sensing", Nano Lett.. 14,1, (2014), 231-238.

Rabiei, Payam, "Heterogeneous lithium niobate photonics on silicon substrates", Optics Express 25573, vol. 21, No. 21, (2013), 9 pgs.

Weigel, Peter, "Lightwave Circuits in Lithium Niobate through Hybrid Waveguides with Silicon Photonics", Scientific Reports, (2016), 9 pgs.

U.S. Appl. No. 16/179,470 U.S. Pat. No. 10,725,239, filed Nov. 2, 2018, Mid-Infrared Intergrated Photonics for Chemical Sensing.

U.S. Appl. No. 16/179,502 U.S. Pat. No. 10,591,410, filed Nov. 2, 2018, Flexible Mid-Infrared Photonics for Chemical Sensing.

U.S. Appl. No. 17/325,109, filed May 19, 2021, Raman Photonic Chips for Chemical and Biological Sensing.

"U.S. Appl. No. 17/325,109, Final Office Action mailed Jan. 19, 2023", 23 pgs.

"U.S. Appl. No. 17/325,109, Non Final Office Action mailed Jun. 16, 2022", 24 pgs.

"U.S. Appl. No. 17/325,109, Response filed Nov. 16, 2022 to Non Final Office Action mailed Jun. 16, 2022", 10 pgs.

De, Vos K, et al., "Silicon-on-Insulator microring resonator for sensitive and label-free biosensing", Opt. Express 15, (2007) (Year: 2007), (2017), 7610-7615.

Qiu, Guangyu, et al., "Dual-Functional Plasmonic Photothermal Biosensors for Highly Accurate Severe Acute Respiratory Syndrome Coronavirus 2 Detection", 14(5):doi: 10.1021/acsnano. 0c02439. Epub Apr. 13, 2020. PMID: 32281785; PMCID: PMC7158889 (Year: 2020), (May 26, 2020), 11 pgs.

* cited by examiner

MID-INFRARED INTEGRATED PHOTONICS FOR BIOLOGICAL SENSING

PRIORITY

This application claims the benefit of priority to U.S. Provisional Application Ser. No. 63/027,095, filed May 19, 2020, which are incorporated by reference herein in their entirety.

TECHNICAL FIELD

The present disclosure relates generally to sensors for biological analytes, e.g., for use in molecular diagnostics.

BACKGROUND

Molecular diagnostics provides techniques for analyzing biological samples, such as blood, urine, or tissue, for the presence or concentration of biological markers in the genome or proteome that are indicative viral or bacterial infections, cancer, or other diseases. Among these techniques are, for example, polymerase chain reaction (PCR) and its variant reverse-transcript PCR (RT-PCR), which serve to selectively amplify specific deoxyribonucleic acid (DNA) or ribonucleic acid (RNA) target sequences, and can be used in conjunction with fluorescence spectroscopy to detect and quantify those genetic targets. Molecular testing for diseases usually involves complex processes and equipment, and is therefore usually performed in centralized medical laboratories, which entails substantial cost as well as delay between the time the sample is taken from a patient and the time the results are available. Efforts have been made to develop techniques that facilitate testing directly at the point of care, i.e., the time and place of patient care.

BRIEF DESCRIPTION OF THE DRAWINGS

Disclosed herein is a photonic biosensing platform that facilitates mid-infrared (mid-IR) absorption spectroscopy of biological samples. Various aspects and example embodiments are described with reference to the accompanying drawings, in which.

DESCRIPTION

Disclosed herein are photonic sensors and associated sensing systems and methods that enable the analysis of biological samples for the presence of biologically active molecules of interest, herein biological "analytes" or "targets," based on specific binding and absorptions in the mid-IR wavelength regime; these sensors are herein also referred to as photonic biosensors. In various embodiments, the sensors include mid-IR-transparent optical waveguides, surface-functionalized with a suitable biological probe layer to bind to a specific biological target. Examples of such biological targets include oligonucleotides (short DNA or RNA molecules) and proteins like enzymes, antibodies, or antigens. Light coupled into the waveguide at an input end generally undergoes wavelength-dependent absorption due to interactions of its evanescent field with molecules bound to or in the vicinity of the waveguide surface, and the resulting absorption spectrum can be measured at the output end of the waveguide. When the biological target is bound to the biological probe, the absorption spectrum generally differs from the spectrum in the absence of the target, facilitating detection. Many biological (as well as chemical) analytes exhibit strong characteristic absorptions at mid-IR wavelengths, rendering that wavelength regime particularly suited for analyte detection.

Photonic biosensors as described herein are amenable to integration into chip-scale sensing platforms, which provide size and cost advantages compared with the table-top equipment conventionally used to detect analytes. Applied to the detection of molecular disease markers, these chip-scale sensing platforms can, in some embodiments, enable moving diagnostics from centralized laboratories to the point of care. Further, the specificity of the biological probe to the target allows isolating the target from any background in the sample by cleaning the sensor surface once the target is bound to the surface. As a result, the disclosed photonic biosensors may enable detecting even small concentrations of the target in the sample that is initially applied to the sensor; in other words, the sensitivity for target detection is high. In the context of detecting oligonucleotides, the high sensitivity may, in some embodiments, allow omitting amplification steps like PCR or RT-PCR.

Figure 1A:
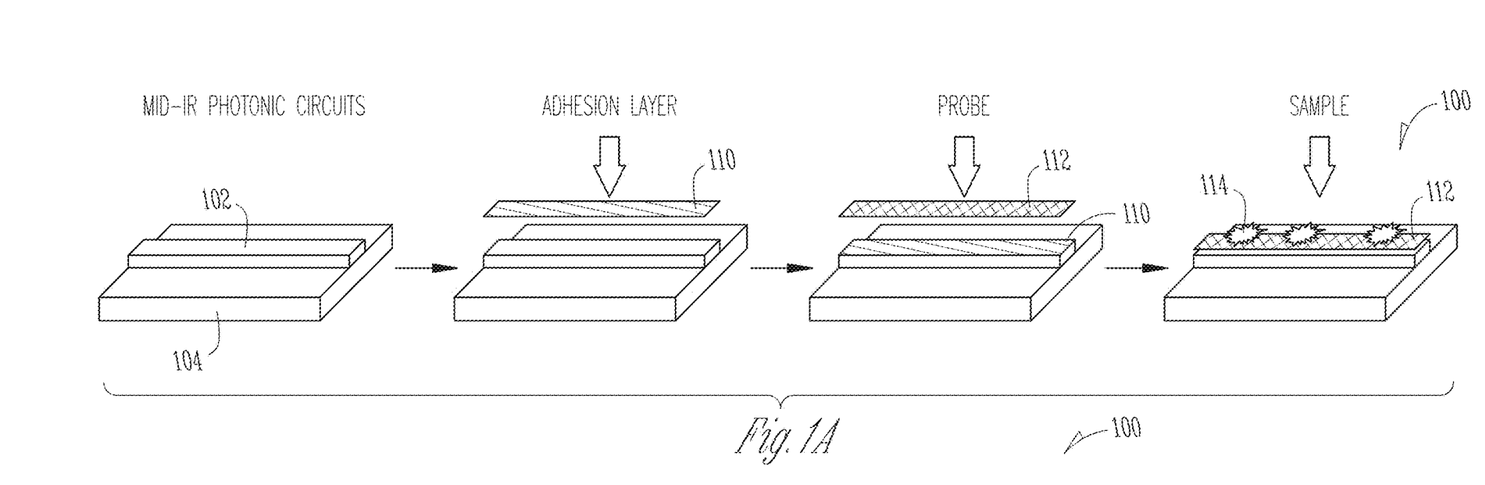
FIG. 1A is a sequence of schematic perspective views showing the preparation of a waveguide-based biosensor in accordance with various embodiments.
Figure 1B:
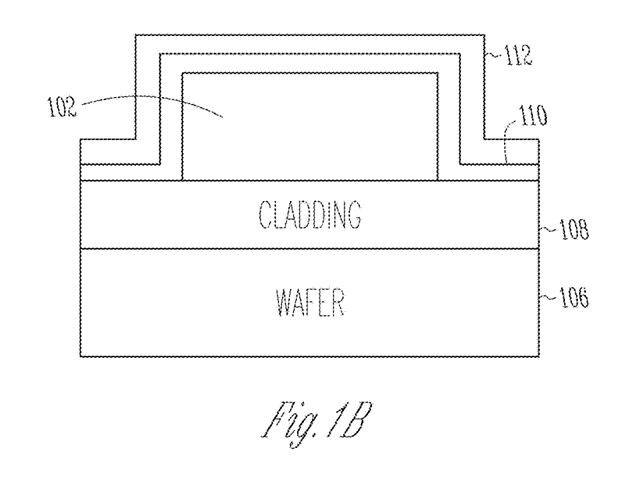
FIG. 1B is a schematic cross section of the waveguide-based biosensor of FIG. 1A.

FIG. 1A is a sequence of schematic perspective views showing the preparation of a waveguide-based biosensor 100 in accordance with various embodiments, and FIG. 1B shows the resulting structure in a schematic cross section. The biosensor 100 includes an optical waveguide 102 formed on a substrate 104. As shown, the waveguide 102 may be a strip waveguide (or, alternatively, rib waveguide), e.g., having a rectangular cross section (although other cross-sectional shapes are also possible) and an aspect ratio of width to height between 1.5 and 3. In some embodiments, the waveguide 102 has a thickness or height between 200 nm and 1 µm, and a width between 0.5 µm and 3 µm. The substrate 104 may include handle layer (wafer) 106 and, disposed on the handle layer 106 (e.g., made of silicon), a cladding layer 108 serving as the undercladding to the waveguide 102.

The waveguide 102 and undercladding 108 can be implemented in various material platforms. In general, the materials of the waveguide 102 and/or the cladding layer 108 are selected to provide a high refractive-index contrast to achieve strong confinement of the optical mode guided in the waveguide 102, as well as to exhibit high transparency to mid-IR light across a specified, generally application-dependent wavelength range, such that light within that range can propagate along the waveguide substantially unattenuated. In some embodiments, the waveguide structure is implemented in standard photonic material platforms, such as silicon (Si) on insulator (SOI) (with silicon oxide ($SiO_2$) being a common insulator material for the undercladding 108); silicon on sapphire (SOS); or silicon nitride (SiNs) on silicon oxide or sapphire. Silicon and silicon nitride are IR-transparent up to about 8 µm, and silicon oxide and sapphire are transparent up to about 3.8 µm and 4.5 µm, respectively, which is suitable for many applications. For example, many analytes may be detected based on the characteristic absorptions of certain chemical functional groups, such as the —CH and —OH groups, which absorb strongly in the 3.0-3.2 µm range and the 2.8-2.9 µm range, respectively. With refractive indices at these mid-IR wavelengths of about 3.5 for silicon, about 2.0 for silicon nitride, about 1.5 for silicon dioxide, and about 1.7 for sapphire, the above material combinations also provide good refractive-index contrast between waveguide 102 and undercladding 108.

Mid-IR transparency over an extended range can be achieved using certain less common material platforms. For instance, a germanium (Ge) waveguide 102 can be formed directly on a silicon substrate 104 (in which case a separate undercladding layer is not needed), with an index contrast of 4 (for germanium) to 3.5. Beneficially, germanium and silicon both provide high transmittance to IR wavelengths to about 8 µm. In other embodiments, a waveguide 102 made of silicon, germanium, or silicon nitride, all of which are transparent (at greater than 95% transmittance) to mid-IR light from about 2.5 µm to about 8 µm, is paired with an undercladding 108 made from barium titanate ($BaTiO_3$, herein also "BTO") or aluminum nitride (AlN), whose IR-transparent windows extend beyond those of $SiO_2$ and sapphire, with BTO exhibiting high IR transmittance from about 2.5 µm to about 7 µm, and AlN from about 2.5 µm to about 9 µm. The material of the handle 106, on which the undercladding 108 is formed, can be, e.g., lanthanum aluminate (LAO) or silicon, and may be selected based at least in part on the undercladding.

For example, in one embodiment, the waveguide structure is implemented using an amorphous-silicon (a-Si) waveguide 102 on an epitaxial BTO thin-film undercladding 108 grown on an LAO wafer providing the handle 106. This material combination provides multiple benefits. In addition to having a broad IR-transparent spectrum, BTO and silicon, with refractive indices of 2.4 and 3.5, respectively, have a high refractive-index contrast. Further, BTO has high chemical stability and mechanical hardness, and can be grown epitaxially on the LAO wafer using various thin-film deposition techniques, with BTO thin films grown on LAO having been shown to provide good crystallinity and in-plane alignment at thicknesses from about 0.25 µm up to 5 µm. The use of amorphous (rather than crystalline) silicon for the waveguide relieves the crystal-lattice-matching constraint between the silicon waveguide and BTO undercladding, allowing an a-Si layer to be directly deposited on the BTO film and then patterned using a standard complementary metal-oxide-semiconductor (CMOS) process. It has been experimentally shown that this fabrication process can achieve a-Si-on-BTO waveguides with well-defined ridge profiles and sharp facets (without bending or distortion on the edge, or cracks or indents on the waveguide surfaces or BTO film) as well as homogeneous composition of both waveguide and BTO film. These characteristics ensure low optical scattering or other propagation losses of light guided in the waveguide.

In another embodiment, the waveguide 102 is implemented in amorphous-silicon (a-Si) on an AlN thin-film undercladding 108 grown on a silicon wafer forming handle layer 106. This material combination provides similar benefits as a-Si-on-BTO, including high transmittance at wavelengths from 2.5 µm to 9 µm, high refractive-index contrast and thus good optical-mode confinement in the waveguide, mechanical strength, thermal stability, and chemical resistance. From a fabrication standpoint, AlN is beneficial in that it can be sputtered onto the wafer at room temperature.

The waveguide 102 can be created in a suitably layered wafer using standard CMOS processes, including combinations of (e.g., photolithographic) patterning and etching. For example, in an SOI platform, the top silicon device layer of the SOI wafer (e.g., including a silicon handle, silicon oxide cladding layer, and silicon device layer) can be photolithographically patterned to define the waveguide (with photoresist covering the area where the waveguide is to be formed), and then etched to remove the silicon in areas surrounding the waveguide. For advanced platforms such as a-Si-on-BTO or a-Si-on-AN, a more complex, but still CMOS-based process may employed. To create a layered wafer for a-Si-on-BTO, a thin epitaxial film of BTO may be grown on a single-crystal LAO substrate, e.g., using pulsed laser deposition, followed by annealing. For a-Si-on-AlN, a thin AlN film may be deposited on a silicon (or other) substrate, e.g., by room-temperature direct current (DC) sputtering. A thin (e.g., 1 µm thick) a-Si film is then grown or otherwise deposited on the respective cladding, e.g., by plasma-enhanced chemical vapor deposition. On this layered wafer, the complement of the waveguide may be defined photolithographically in a patterned photoresist layer, which can then be used to create a mask (e.g., made of chromium) by electron beam evaporation, followed by lift-off of the photoresist layer along with the mask material deposited thereon. The mask defining the structure of the waveguide can then be transferred to the a-Si device layer, for instance, by reactive ion etching, which allows creating sharp a-Si waveguide facets and smooth cladding surfaces and cladding-waveguide interfaces, as are important to minimize propagation and scattering losses. The waveguide structure is finalized by removing the remaining mask material and any other residue on the device surface, e.g., using ceric ammonium nitrate solution, followed by an oxygen plasma ashing process.

With renewed reference to FIGS. 1A and 1B, to functionalize the waveguide 102 for biological targets, it may be coated by a thin adhesion layer 110, followed by a biological probe layer 112. The adhesion layer 110 may be made of a material with two chemical functional groups that can bond to the waveguide surface and to the biological probe forming the probe layer 112, respectively. In some embodiments, the adhesion layer 110 is made from a reactive silane, e.g., of the formula $R^1$—$Si(OR^2)_3$, wherein $R^1$ is an aminoalkyl group and each $R^2$ is, independently, a ($C_1$-$C_6$)alkyl group; in one example, the reactive silane is or includes (3-aminopropyl) trimethoxysilane (APTMS). The adhesion layer 110 may be applied to the waveguide surface by spin-coating.

The biological probe layer is made up of biological molecules (e.g., proteins or polynucleic acid) that act as a biological "capture agent" in that they will selectively bond to the target 114 when the coated waveguide is wetted with a sample including the target 114. To create the probe layer 112 on top of the adhesion layer 110, a solution including the biological probe or capture agent (herein used synonymously) is applied to the adhesion layer (e.g., by simply creating a drop of the solution on top of the adhesion layer), and the biological probe then binds (on its own) to the adhesion layer 110. Application of the biological probe 112 on top of the adhesion layer 110 may form a reaction product bound to the waveguide surface. Alternatively to adhering the biological probe to the waveguide via an adhesion layer 110, the probe layer 112 may also be formed directly on the waveguide surface, e.g., bonding with the surface due to electrostatic forces, and the adhesion layer 110 may, accordingly, be omitted. To facility such direct bonding, the waveguide surface and/or the solution including the biological probe may be pre-modified. For example, the pH of the probe solution may be adjusted to encourage bonding of the biological probe to the waveguide. The thickness of the probe layer 112, or the adhesion layer 110 and probe layer 112 together, may be in the sub-nanometer range, or up to a few hundred nanonmeters (e.g., 400 nm), depending on the type of biological probe used.

The capture agent that makes up the probe layer 112 is selected, based on the application, to bind specifically to the target. The capture agent may, for instance, bond to biological moieties located on the surface of viruses, bacteria, or fungi. For example, in some embodiments, the target is an antigen, and the capture agent includes the associated antibody. In other embodiments, the target is a DNA or RNA molecule associated with a specific gene, and the capture agent includes DNA having the complementary nucleotide sequence. In one example embodiment, the biological probe is made from proteins or DNA that will only bond to a target, such as DNA or antibodies, related to a coronavirus (e.g., SARS-CoV-1, which caused the SARS outbreak in 2003, or SARS-CoV-2, which caused the current COVID-19 pandemic starting in 2019). The sensing mechanism employed by the waveguide-based biosensor is illustrated in FIGS. 2 and 3A-3B.

Figure 2:
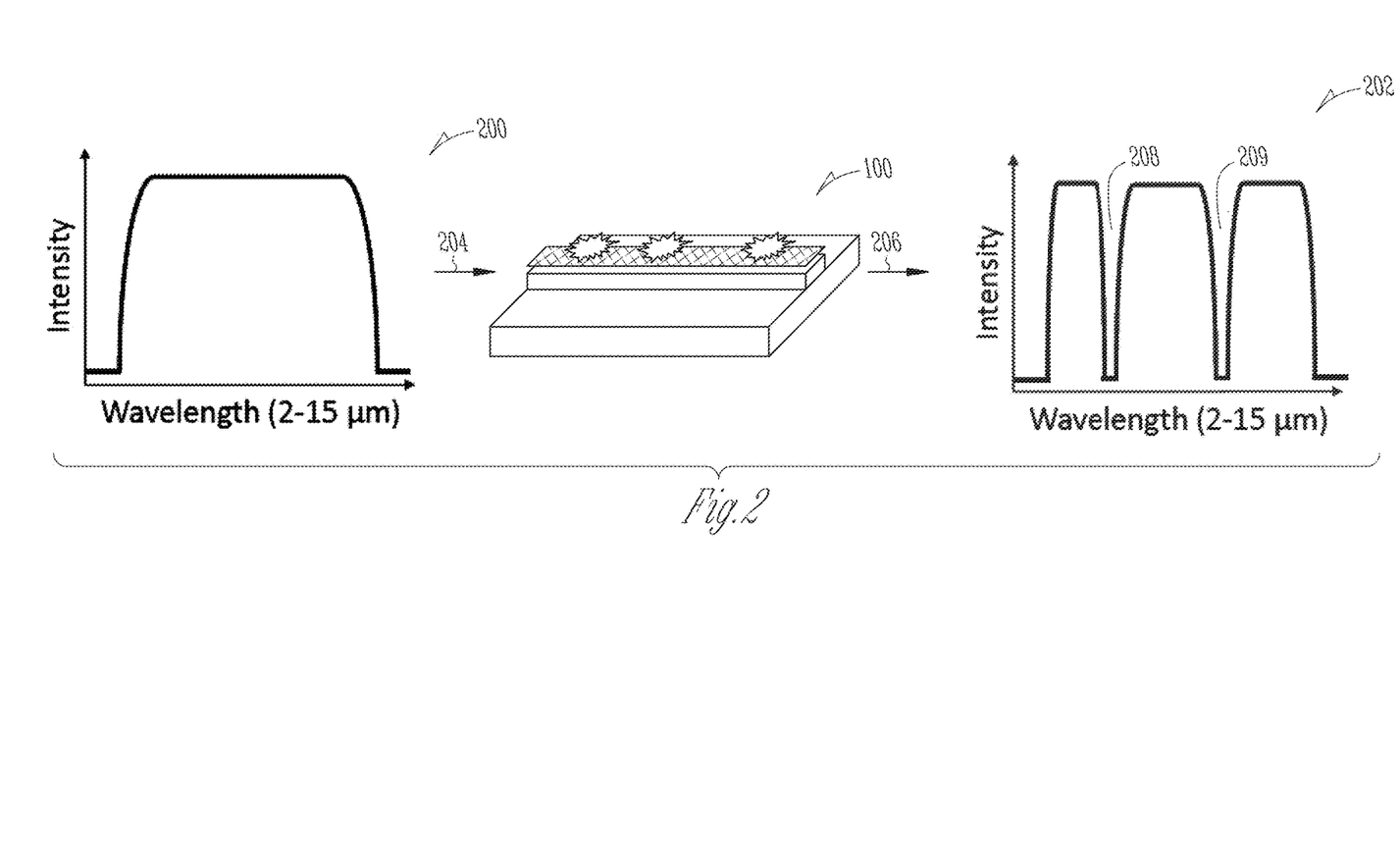
FIG. 2 is a schematic perspective view of the waveguide-based biosensor of FIGS. 1A and 1B, along with schematic input and output IR spectra.

FIG. 2 is a schematic perspective view of the waveguide-based biosensor 100 of FIGS. 1A and 1B, along with schematic input and output IR spectra 200, 202 (plotted as light intensity vs. wavelength). Note that the biosensor 100 shown is the surface-modified portion of a generally longer waveguide 102, which, in turn, may be part of a larger photonic circuit. In IR absorption spectroscopy, broadband or narrowband mid-IR light 204 is coupled into the waveguide 102 at one end (constituting the waveguide input), and the light 206 that is transmitted at the other end (constituting the waveguide output) is measured to detect any absorptions. In the schematically depicted example, the input spectrum 200 is broadband, covering the mid-IR range from about 2 μm to about 15 μm, and the output spectrum 202 depicts drops in intensity 208, 209, corresponding to absorption peaks, at two characteristic wavelengths. In general, the number, magnitude, and width of the absorption peaks varies depending on the local environment with which the sensor 100 interacts. Note that, to measure the various wavelength components, the photonic circuit may include micro-resonators, photonic crystals, or other optical structures that spread out the spectrum. In some embodiments, the biological probe layer extends to these components, so that they become part of the biosensor.

To use the biosensor 100 to test a liquid sample (e.g., taken from a patient, or prepared from a specimen taken from the patient) for the target, the biosensor 100 is first wetted by the liquid sample, and the sensor surface is thereafter cleaned (e.g., rinsed with water), leaving only molecules that can bind to the probe—by design ideally only the target-bound to the sensor surface. The mid-IR spectrum measured at the output of the waveguide sensor will generally differ between samples with and without target, with samples including the target exhibiting additional absorptions. Since these absorptions are generally signature absorptions, e.g., associated with certain chemical groups present in the target, the sensor provides high detection accuracy. Further, the sensor length, that is, the length of the waveguide portion covered with the probe, can generally be made sufficiently long to offer high sensitivity for target detection; in practice, sensor lengths may range from tens of micrometers to centimeters.

Figure 3A:
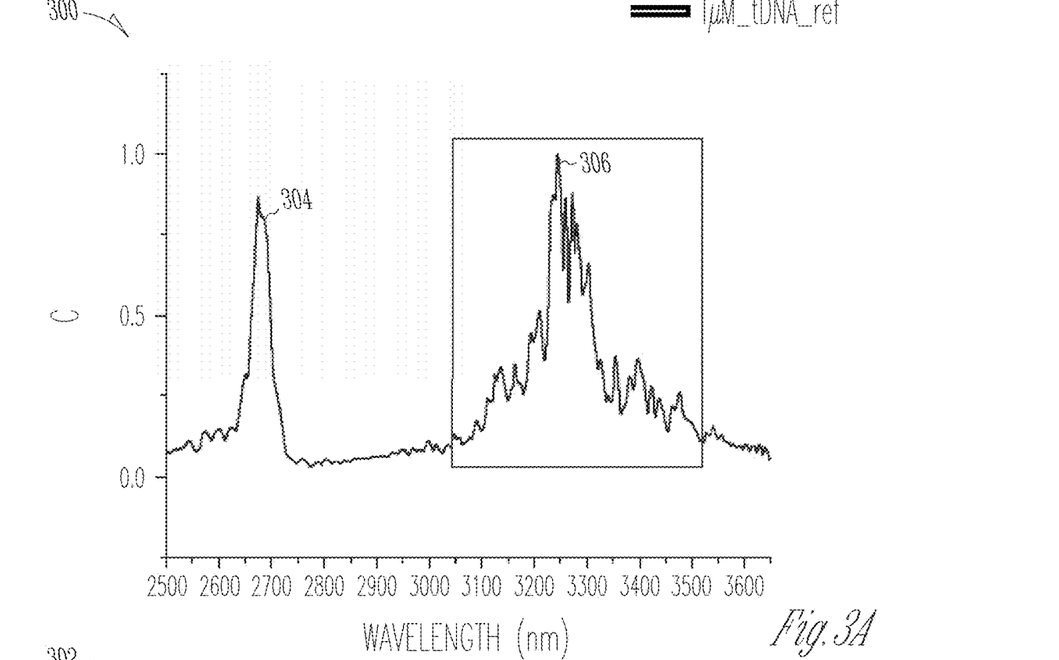
FIGS. 3A and 3B are example IR spectra acquired from a waveguide-based biosensor in the absence and presence, respectively, of coronavirus target DNA, in accordance with an embodiment.
Figure 3B:
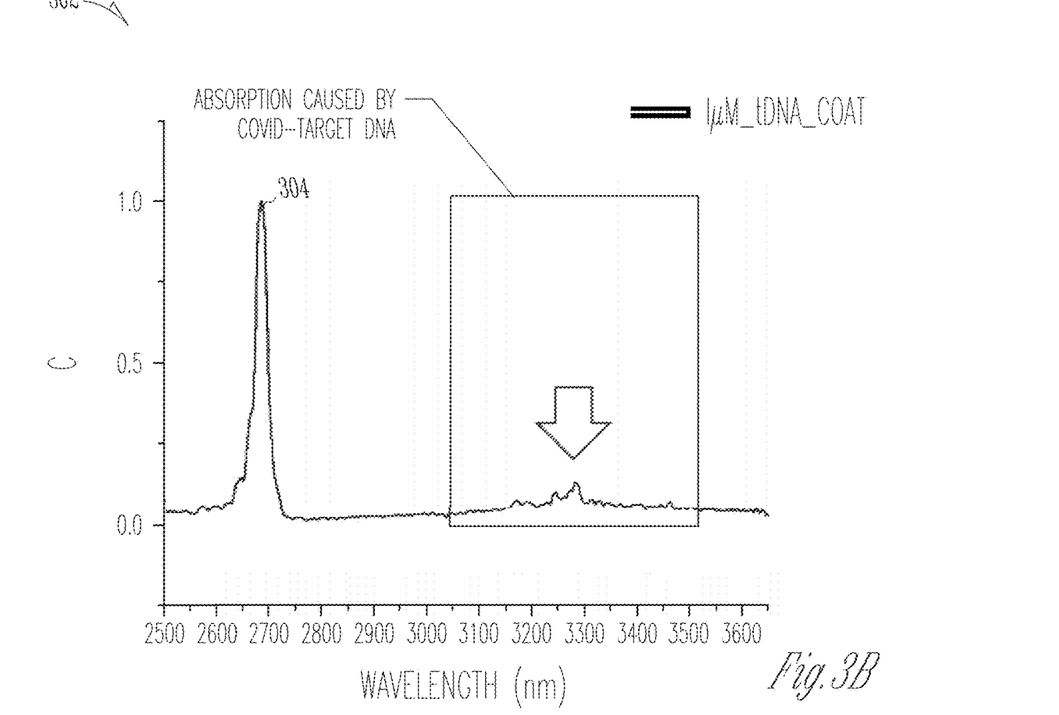

FIGS. 3A and 3B are example IR spectra 300, 302 acquired from a waveguide-based biosensor in the absence and presence, respectively, of coronavirus target DNA or RNA, in accordance with an embodiment. More specifically, the target in this measurement was the 2019-nCoV N1 marker gene, one of two specific regions in the SARS-CoV-2 nucleocapsid (N) gene that is commonly tested for, conventionally using real-time (RT-)PCR, to diagnose COVID-19. The probe layer 112 of the biosensor 100 contained the DNA sequence 5' GGT CCA CCA AAC GTA ATG CGG GGT-3' which serves as the capture agent for the 2019-nCoV N1 marker gene. As can be seen in FIG. 3A, in the absence of the COVID target DNA, the mid-IR transmission spectrum 300 includes two peaks 304, 306 at 2700 nm and 3300 nm, corresponding to wavelengths at which the surface-modified waveguide does not absorb substantially. In the presence of COVID target DNA, as shown in FIG. 3B, the peak 306 at 3300 is largely absorbed. This absorption is related to the C—H band absorption. FIGS. 3A and 3B provide evidence that the COVID target DNA can be accurately detected using the bionsensor 100 disclosed herein.

Having described a waveguide-based biosensor itself, along with its principle sensing mechanism, the larger sensing system will now be described.

Figure 4A:
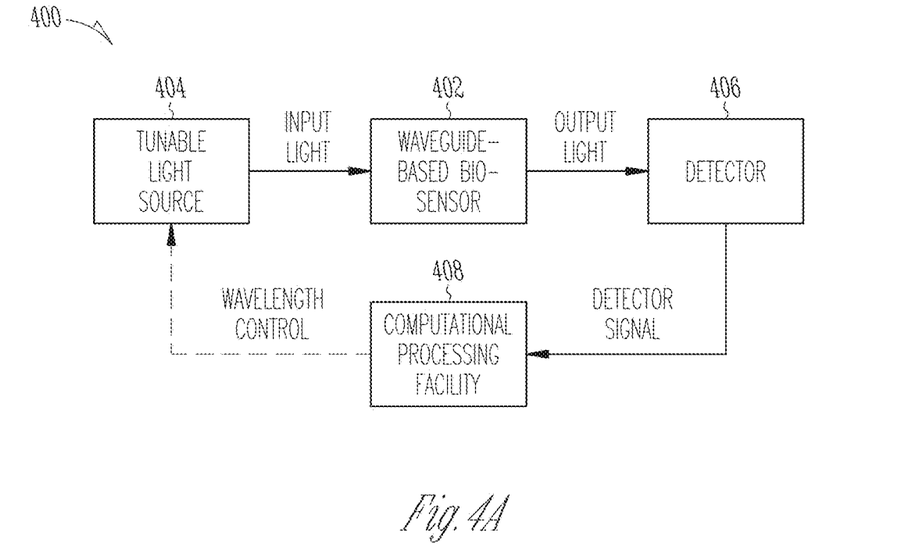
FIGS. 4A and 4B are block diagrams of IR absorption spectroscopy systems incorporating a waveguide-based biosensor, in accordance with various embodiments.

FIGS. 4A and 4B are block diagrams of IR absorption spectroscopy systems incorporating a waveguide-based biosensor (e.g., sensor 100 of FIGS. 1A and 1B), in accordance with various embodiments. Shown in FIG. 4A is a system 400 that includes, in addition to the waveguide-based biosensor 402, a tunable mid-IR light source 404 (e.g., a tunable laser) coupling light, directly or indirectly, into the sensor 402, a mid-IR detector 406 measuring the light exiting the sensor 402, and a computational processing facility 408 that processes the measured signal. The computational processing facility 408 may be implemented in analog or digital circuitry; if the latter, the electronic output of the detector 406 may be converted into a digital signal by an analog-to-digital converter (not shown). In some embodiments, the computational processing facility 408 is provided by a programmable processor (e.g., a field-programmable gate array (FPGA) or general-purpose central processing unit (CPU)) executing suitable software.

The light source 404 is tunable over an operating wavelength range of the sensing system 400, facilitating measurements of absorption spectra, across that wavelength range, of samples in contact with the sensor 402 and detection of targets with characteristic absorptions at wavelengths within that range. In some embodiments, the operating wavelength range extends from about 2.5 µm or less to at least about 3.8 µm, at least about 4.5 µm, or at least about 7 µm. The detector 406 may be, for instance, a photodetector that measures the overall intensity of the light output by the waveguide sensor 402, or, alternatively, a camera (e.g., an array of photosensors) that allows imaging the optical mode at the waveguide sensor output. Either way, the detector 406 is selected or configured to be sensitive to light within the operating wavelength range. In various embodiments, for instance, an indium antimonide (InSb) infrared camera, which is responsive to light from less than 1 µm up to 5.3 µm, or an HgCdTe (MCT) camera, which is sensitive up to at least 7 µm, is used. The computational processing facility 408 may be configured to create a spectrum by associating the measured output signal of the sensor 402 at a given time with the respective wavelength input by the light source 404 at that time. The computational processing facility 408 may have knowledge of the light-source wavelength by virtue of controlling the tunable wavelength itself, or by receiving a signal indicative of the wavelength from a separate light-source controller (not shown). In addition to computing a spectrum, the computational processing facility 408 may also implement processing logic for analyzing the spectrum, e.g., to determine characteristic absorptions and link them to a specified target if applicable.

Figure 4B:
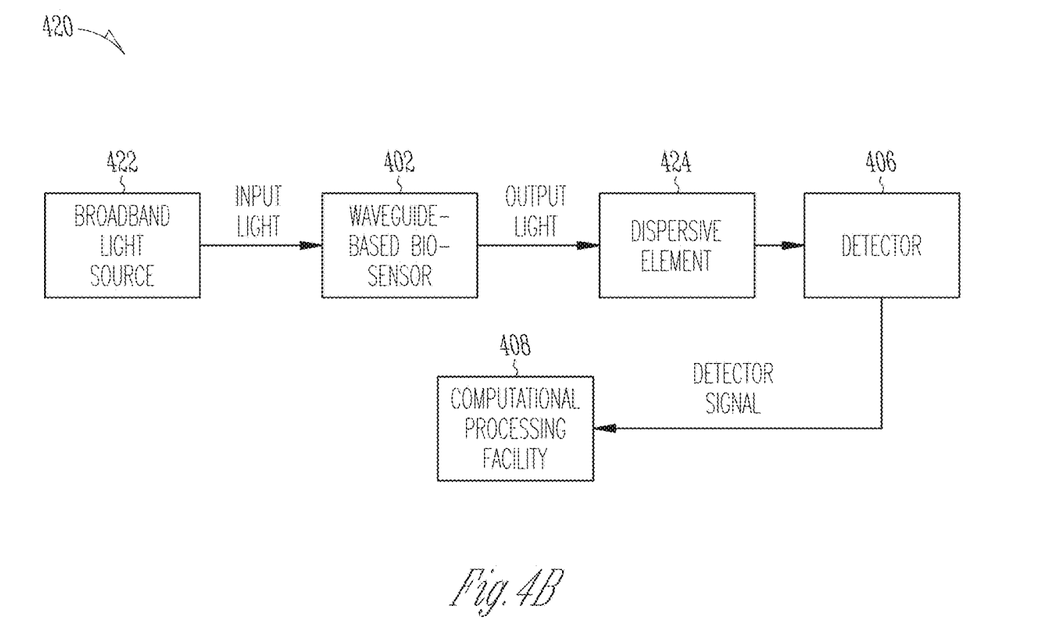

FIG. 4B shows an alternative sensing system 420 including, instead of a tunable light source, a broadband light source 422 providing light covering the operating wavelength range. To facilitate the acquisition of a spectrum, the system 420 may further include a dispersive element 424 at the output of the waveguide-based biosensor 402, preceding the detector(s) 406, to spatially spread out the light by wavelength. For instance, as noted above, the system 420 may include microresonators, photonic crystals, and the like to achieve the wavelength dispersion. Using a camera as the detector 406, the output intensity at different wavelengths can then be measured at different respective locations within the sensor array of the camera. Alternatively to a camera, multiple photodetectors (e.g., a photodiode array detector) may be placed at different locations corresponding to different respective wavelengths, or a single detector (or camera) may be moved to measure the intensity for different wavelengths. In a broadband-light sensing system 420, the computational processing facility 408 generates a spectrum by associating the location of the measured light intensity with wavelength.

In both sensing systems 400, 420, the light emitted by the light source 404, 422 may be collimated, e.g., with a refractive lens, into an optical fiber, which may then be butt-coupled to the waveguide sensor 402. Similarly, the light output by the waveguide sensor 402 may be focused by a lens (e.g., a barium fluoride biconvex lens) onto the camera or other detector 406. Alternatively, the light source 404, 422 and/or detector 406 may be implemented as photonic-circuit components and monolithically integrated with the sensor 402 on the same substrate. Lasers and detectors may be formed, e.g., by silicon device structures (which may be created in the same layer, and using the same or similar methods, as used for the creation of the waveguide 102 of the biosensor) in conjunction III-V structures serving as active regions and associated electrodes, which may likewise be patterned using standard CMOS processes. Suitable photonic-component structures and manners of manufacturing same are well-known to those of ordinary skill in the art. To provide just one example, in some embodiments, a quantum cascade laser, which can emit light in the mid-IR regime, may be used as the light source. If integrated as photonic-circuit components, the light source 404, 422 and sensor 406 may directly couple to a waveguide a portion of forms part of the waveguide-based biosensor 402.

Figure 5:
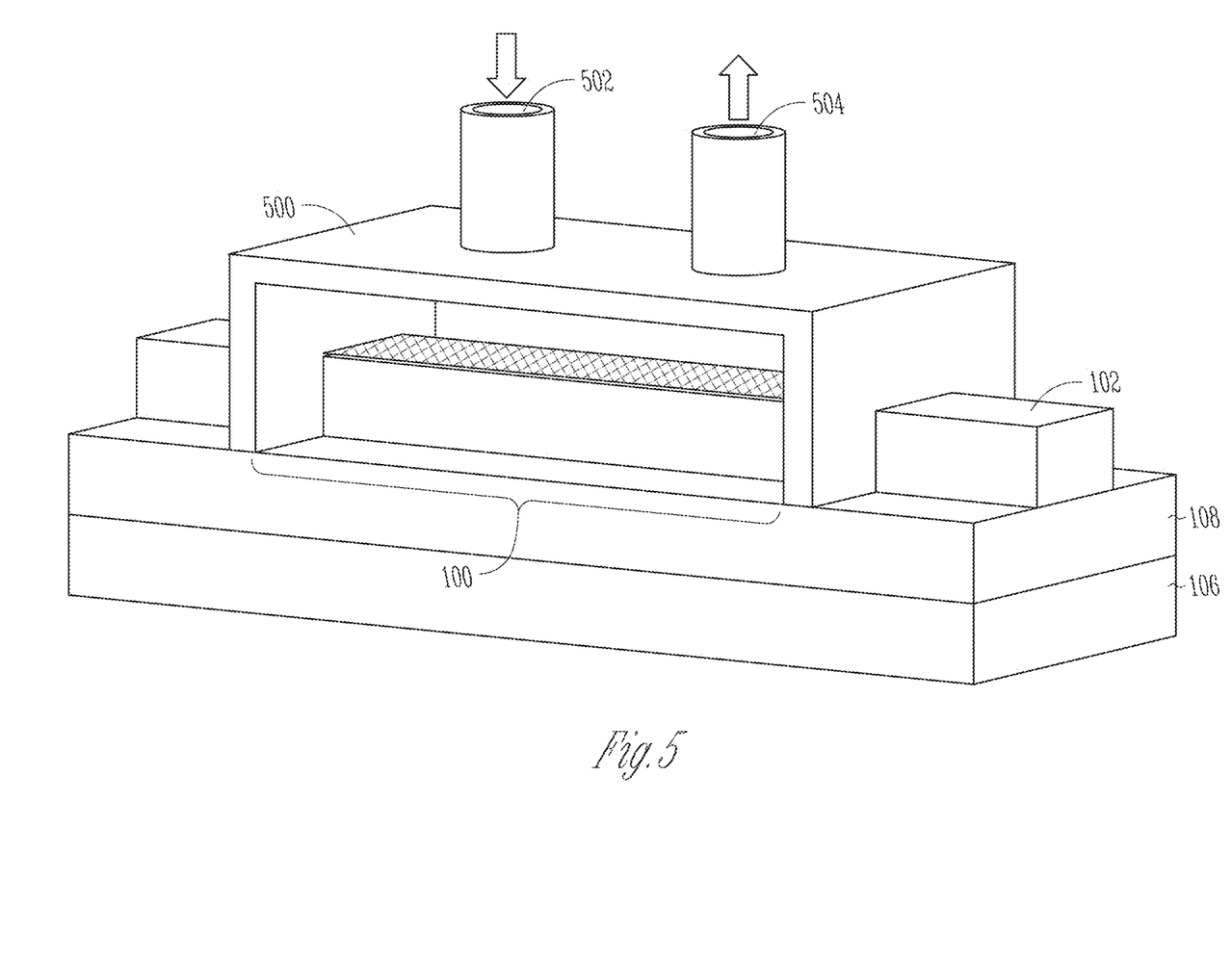
FIG. 5 is a cut-away perspective view of a waveguide-based biosensor enclosed in a microfluid chamber in accordance with various embodiments.

To perform mid-IR absorption spectroscopy on a sample, the sample may be dispensed onto the waveguide-based sensor 100, 402 using a pipette, syringe, or similar tool, e.g., to form a drop on top of, or surrounding a portion of the top and side facets, of the surface-modified waveguide. Alternatively, the sample may be applied using microfluids. This is shown conceptually in FIG. 5, which provides a cut-away perspective view of a waveguide-based biosensor 100 enclosed in a microfluid chamber 500 in accordance with various embodiments. As can be seen, the microfluidic chamber 500 is formed on top of the photonic chip, enclosing the surface-modified portion of the waveguide 102, and includes a fluid inlet 502 and fluid outlet 504 that allow sample to be pumped through the chamber 500. Following application of the sample, the microfluidic chamber 500 can also be used to rinse and clean the sensor surface. The microfluidic chamber 500 may be formed, e.g., from a polymeric organosilicon such as polydimethylsiloxane (PDMS), or from some other suitable material. Methods for fabricating opto-fluidic chips including microfluidic components above a photonic circuit chip are known to those of ordinary skill in the art.

Waveguide-based biosensors as described herein lend themselves to the quick analysis of individual samples, e.g., immediately upon obtaining the sample from a patient at the point of care. On the other hand, they are also amenable to use in large numbers, e.g., integrated on a single chip in an array and optionally each provided with a microfluidic chamber holding the sample, for simultaneous measurements of multiple samples in high-throughput applications. In the latter case, multiple waveguide-based sensors may receive input light from separate respective (e.g., on-chip) light sources, or from a single light source whose output is optically split between multiple channels including the multiple respective sensors. Each sensor may have its own respective associated detector. It is also possible to switch the output of a light source, and similarly the input of a detector, cyclically between multiple respective sensors for sequential measurements with the sensors; the time in between successive measurements with any given sensor can be used to load a new sample into the associated microfluidic chamber, or otherwise bring a new sample into contact with the sensor.

Figure 6:
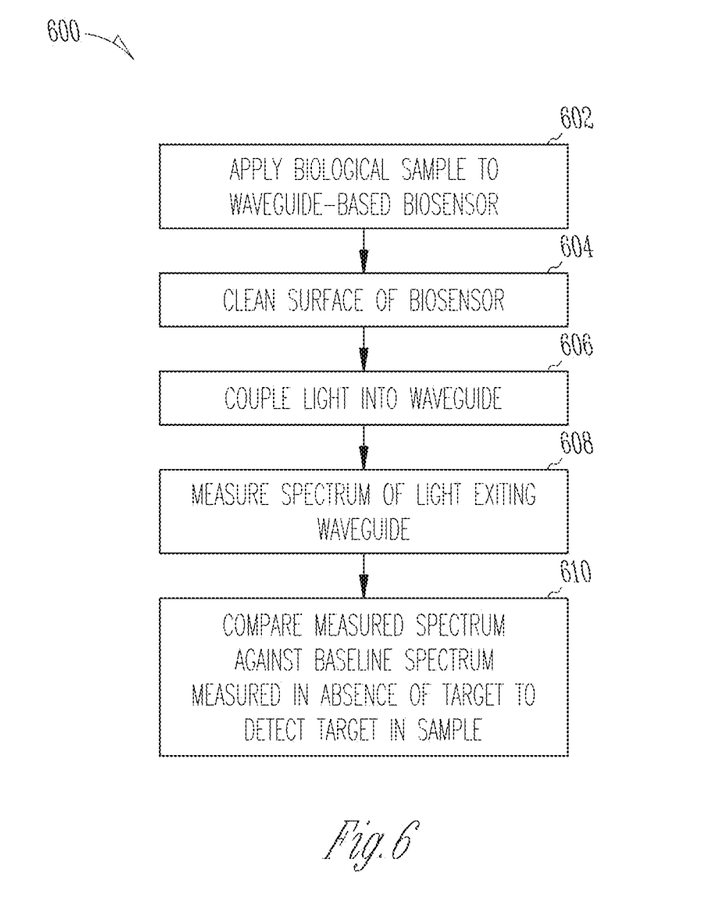
FIG. 6 is a flow chart of a method for waveguide-based biological sensing in accordance with various embodiments.

FIG. 6 is a flow chart of a method 600 for waveguide-based biological sensing in accordance with various embodiments. The method 600 involves applying a biological sample to a waveguide-based biosensor (e.g., sensor 100, 402, or slot-waveguide-based sensor 700 described below) (that is, the portion of the sensor waveguide that is coated with a biological probe) as described herein, e.g., by dispensing a liquid sample from above onto the sensor or flowing the sample across the surface of the sensor (e.g., through a microfluidic chamber formed above the sensor) (act 602). Target molecules 114 contained in the sample will then bind to the probe layer 112 of the sensor, and thus be immobilized on the sensor surface. Following sample application and target binding, the sensor surface is cleaned (act 604) by rinsing off or otherwise cleaning the remaining sample, leaving only the bound target 114 behind on the sensor surface. The target 114 bound to the probe of the sensor can optically interact with the evanescent field of light guided in the sensor waveguide, which may result in characteristic absorptions at certain wavelengths, particularly in the mid-IR regime.

To measure these characteristic absorptions, mid-IR light is coupled (e.g., from a laser light source 404, 422) into the sensor waveguide at one end (act 606), and the light exiting the waveguide at the other end is measured, e.g., with a camera or photodetector (act 608). More specifically, the light is measured spectrally, that is, as a function of wavelength. The spectral resolution of the transmitted light can be achieved, for example, by tuning the wavelength of the light coupled into the waveguide over a specified range, and simultaneously monitoring the intensity of the transmitted light at the output. Alternatively, the light coupled into the waveguide may be broadband, and the wavelengths at the output may be spatially dispersed to facilitate spectral measurements. The optical mode launched into the waveguide sensor may be a fundamental mode, and may be either transverse electric (TE) or transverse magnetic (TM). In certain embodiments, a TM mode is selectively excited in the waveguide, e.g., by virtue of the waveguide geometry and/or the light source. As explained below with reference to FIGS. 9A-9E, for strip waveguides 102, TM modes have been found to exhibit stronger evanescent fields, resulting in stronger interactions of the light with the surrounding sample and, consequently, larger absorption signals. On the other hand, as explained with reference to FIGS. 10A-10E, for slot waveguides, the TE mode achieves significantly higher intensities in the slot than the TM mode, rendering the TE mode preferable to achieve greater light-analyte interaction. Thus, the polarization may be selected based at least in part on the type of waveguide utilized in the sensor.

The measured light (i.e., the generated detector signal) is processed, in act 610, to determine whether any target is present on the sensor. In various embodiments, this determination involves comparing the measured spectrum against a baseline spectrum measured for a control sample that did not include any target, and detecting any absorptions additional to those that occur in the absence of the target due to the probe alone. Further, the wavelengths at which any such additional absorptions are detected may be compared against the expected characteristic wavelengths or wavelength bands at or in which the target is expected to absorb, confirming, if consistent, the accuracy of the measurement. The characteristic wavelengths may, for instance, be associated with certain chemical functional groups contained in the target. For example, —CH absorbs strongly between 3.0 and 3.2 µm, whereas —OH absorbs between 2.8 and 2.9 µm. Further, at longer mid-IR wavelengths (e.g., at wavelengths greater than 6 µm), absorptions due to stretching and bending vibrations (e.g., of C—C, C—O, or C—N bonds) tend to vary with the larger molecular structure. For certain complex (e.g., biological) molecules with multiple stretching and bending absorptions, the absorptions can collectively provide a molecular "fingerprint" that allows identifying the substance.

Figure 7:
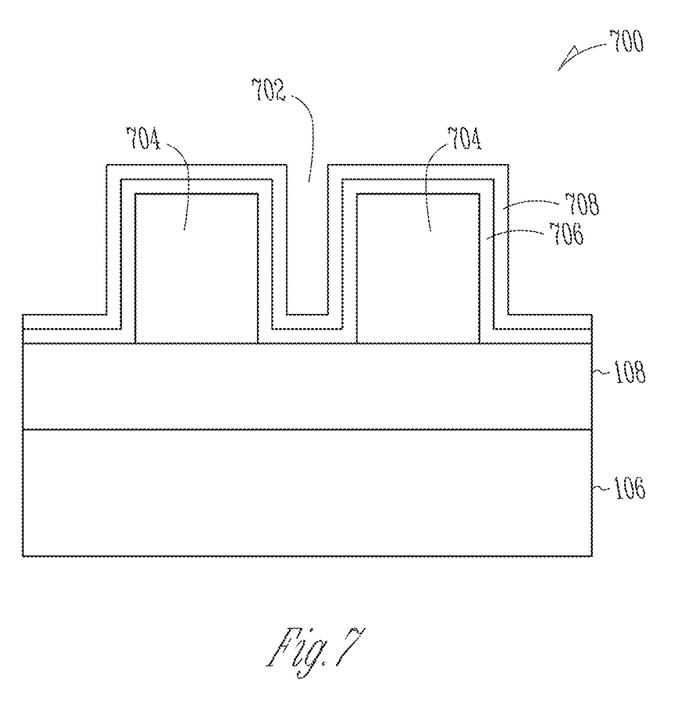
FIG. 7 is a schematic cross section of a biosensor incorporating a slot waveguide, in accordance with various embodiments.

In some embodiments, the sensitivity of the waveguide-based biosensor is enhanced by replacing the strip waveguide 102 with slot waveguide whose sub-wavelength slot doubles as a fluidic channel for the sample. FIG. 7 is a schematic cross section of a biosensor 700 incorporating such a slot waveguide 702, in accordance with various embodiments. The slot waveguide includes a vertical slot 702 centered between two waveguide strips 704. This slot 702 has a width that varies depending on the particular application, but is generally significantly smaller than the mid-IR wavelengths at which the sensor is intended to operate. For example, in some embodiments, the width of the slot is 100 nm or less; the waveguide is, in this case, also referred to as a nano-slot waveguide. In other embodiments, the width of the slot is between 100 nm and 400 nm. The overall waveguide dimensions may be similar to those of the strip waveguide 102, with a width on the order of a micrometer, and an aspect ratio of width to height between about 1.5 and 3. To render the slot waveguide suitable for detecting biological analytes, the waveguide is coated with an optional thin adhesion layer 706 and a probe layer 708 that may include a capture agent for the target. As can be seen, these layers may be disposed over the top and side walls of the waveguide strips 704, thus lining the walls of the slot 702. (Note that FIG. 7 is a conceptional depiction and not drawn to scale. The adhesion and probe layers 706, 708 may, in some embodiments, have thicknesses of only a few nanometers, or even sub-nanometers, much smaller than the width of the slot 702.)

Figure 8:
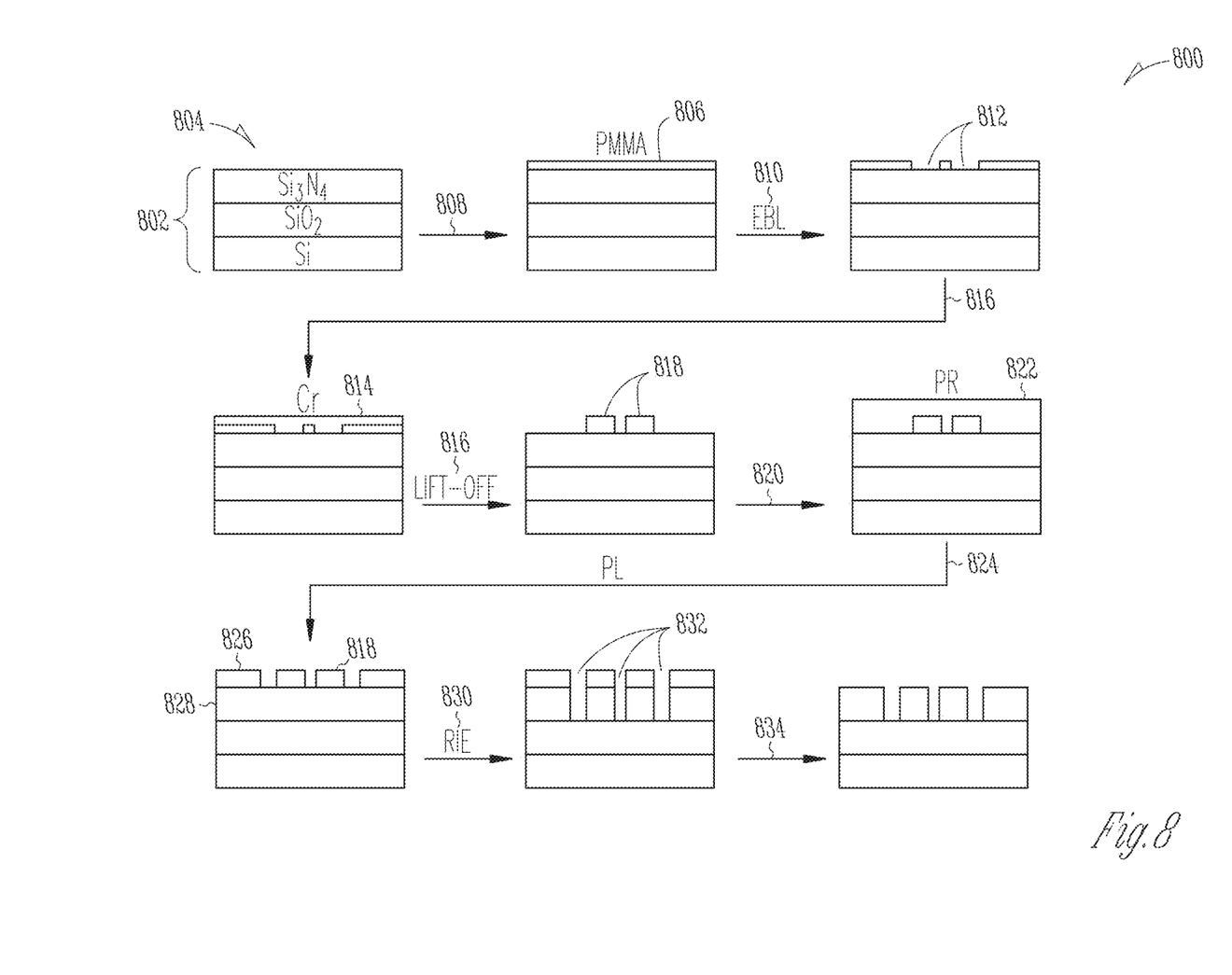
FIG. 8 is a sequence of cross-sectional views of a slot waveguide, as may be used in the biosensor of FIG. 7, illustrating an example method of manufacturing the nano-slot waveguide, in accordance with various embodiments.

FIG. 8 is a sequence of cross-sectional views of a slot waveguide as may be used in the biosensor 700, illustrating an example method 800 of manufacturing the nano-slot waveguide, in accordance with various embodiments. In general, the slot waveguide, along with strip waveguides at its input and output and associated couplers, is created using a multi-step fabrication process, including, e.g., thin-film deposition, lithography, and selective plasma etching. Various material platforms, e.g., as described above with reference to FIGS. 1A and 1B, may be used for the layered wafer 802 in which the waveguide structures are formed. To provide just one example, the waveguide structures may be created in the silicon nitride device layer of a $Si_3N_4$-on-insulator layered wafer, which itself may be made by plasma-enhanced chemical vapor deposition (PECVD) to first form a silicon dioxide layer (e.g., 2-5 µm thick) on a silicon substrate, and thereafter to deposit a $Si_3N_4$ layer (e.g., 400 nm thick) on the silicon dioxide layer, using dilute $SiH_4$ and $N_2$ precursor gases.

In the depicted example process, starting with a layered wafer 802 (at 804), a positive electron beam resist layer 806 (e.g., a double layer of 495K and 950K PMMA A4) is spun on the layered wafer (at 808), and then patterned using electron beam lithography (EBL) (at 810). The portions of the layer 812 that are removed in the process define the slot waveguide. A mask layer 814, e.g., made of chromium (Cr) and about 50 nm thick, is deposited over the patterned substrate, for instance, using electron beam evaporation (at 816). In a lift-off process (at 816), the resist layer 806, along with the portions of the Cr mask layer 814 deposited thereon, is then removed, leaving a patterned Cr mask 818 defining and covering only the regions of the slot waveguide. The device is then (at 820) spin-coated with a layer of (e.g., S1818) photoresist (PR) 822. The photoresist layer 822 is patterned by photolithography (at 824) to define the input and output waveguides and associated couplers, aligned with the EBL-created waveguide slot pattern. The patterned photoresist 826 and Cr mask 818 together expose the surface of the wafer device layer 828 in the regions of the waveguide slot and of channels to be etched into the device layer around and defining the waveguide structures. These devices patterns are transferred into the (e.g., $Si_3N_4$) device layer by selective reactive ion etching (RIE) (at 830), creating channels 832 (including the waveguide slot) in the device layer 828. The Cr mask 818 and patterned photoresist 826 are then removed, using a remover based on, e.g., ceric ammonium nitrate etchant solution and 1-methyl-2-pyrrolidon (NMP). The final structure may include the slot waveguide, input and output strip waveguides, and tapered couplers connecting the input/output waveguides to the slot waveguide. It has been experimentally verified that the described process can achieve clearly defined structures with a smooth top surface, indicating uniform etching with no damage introduced during the RIE process.

Figure 9A:
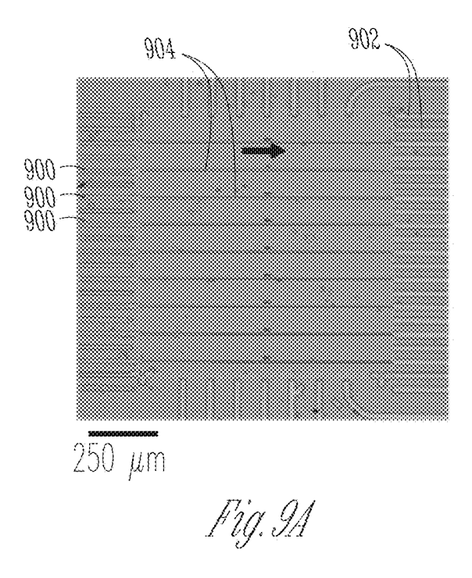
FIGS. 9A-9E are top views of example nano-slot waveguide structures in accordance with an embodiment.
Figure 9B:
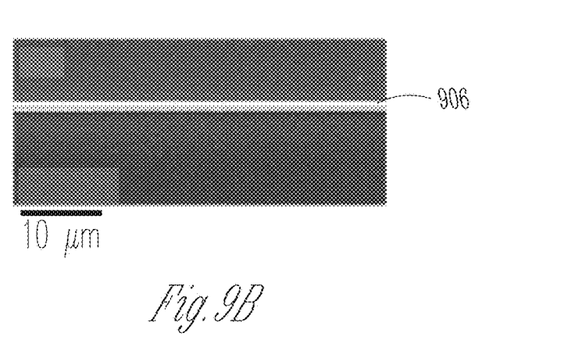
Figure 9C:
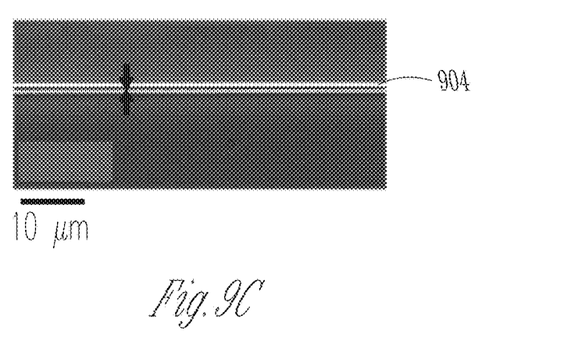
Figure 9D:
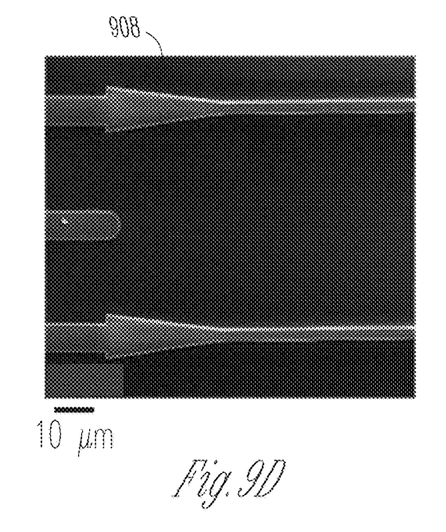
Figure 9E:
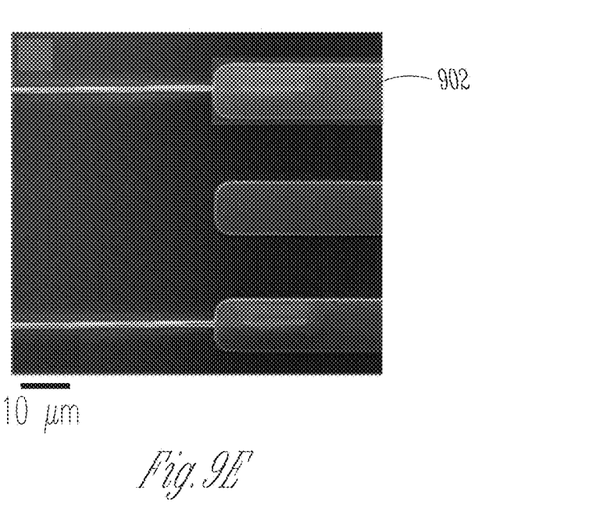

FIGS. 9A-9E are top views of example nano-slot waveguide structures in accordance with an embodiment, individually drawn to scale based on optical microscopy and scanning electron microscopy images. FIG. 9A shows the array of the input and output strip waveguides 900, 902 and the nano-slot waveguides 904 in the center of the devices. FIGS. 9B and 9C show, enlarged, details of a reference strip waveguide 906 and a nano-slot waveguide 904, respectively. The example strip waveguide in FIG. 9B has a width of 0.8 µm, and the example nano-slot waveguide in FIG. 9C has a slot width of 100 nm centered between two 0.4 µm wide $Si_3N4$ strips. FIG. 9D shows, at a higher magnification, the input region, showing a tapered input coupler 910 connecting the input waveguide 900 to the slot waveguide 904. FIG. 9E shows the output region, highlighting the transition from the nano-slot waveguide 904 to a wider output waveguide 902. Accurate alignment between the slot waveguide 904 and the input and output waveguides 900, 902, in a conjunction with the taper coupler 908, ensure the efficient excitation of a nano-slot waveguide mode.

FIGS. 10A-11E illustrate the sensitivity enhancement that can be achieved with nano-slot waveguides, as was evaluated computationally based on optical mode profiles simulated by two-dimensional finite difference method (FDM) for both strip and nano-slot waveguides. The device dimensions of the slot waveguide for the simulation were those shown in FIGS. 9A-9E. The waveguides were formed in $Si_3N_4$ on $SiO_2$. Refractive indices of 2.1 for the $Si_3N_4$ waveguide and of 1.45 for the $SiO_2$ undercladding were used in the simulations, and a 2 µm×0.8 µm excitation source was selected.

Figure 10A:
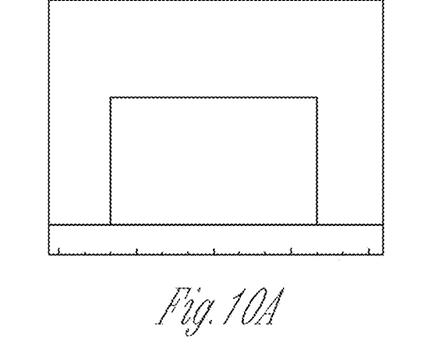
FIG. 10A is a cross-sectional view of a strip waveguide as may be used in biosensors in accordance with various embodiments.
Figure 10B:
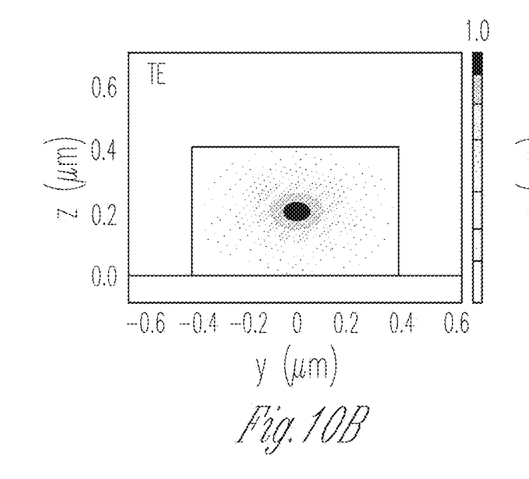
FIGS. 10B and 10C show example optical modes in the strip waveguide of FIG. 10A in two dimensions for transverse electric (TE) and transverse magnetic (TM) polarizations, respectively.
Figure 10C:
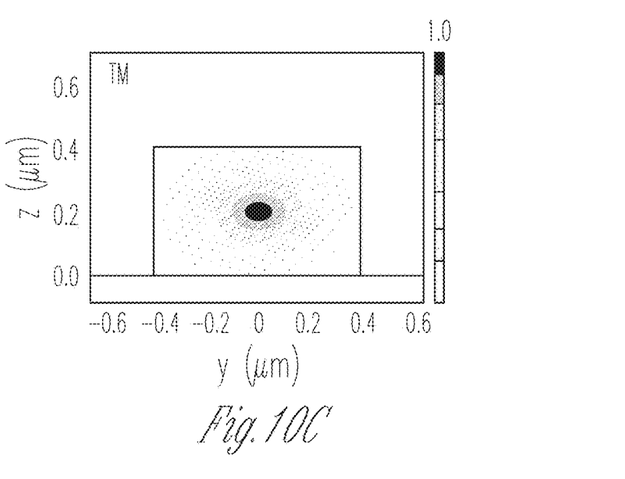
Figure 10D:
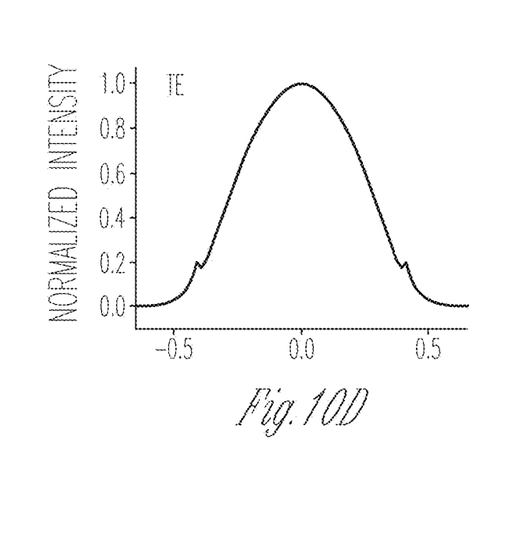
FIGS. 10D and 10E are example one-dimensional profiles of the field distribution associated with the optical modes of FIGS. 10B and 10C, respectively.
Figure 10E:
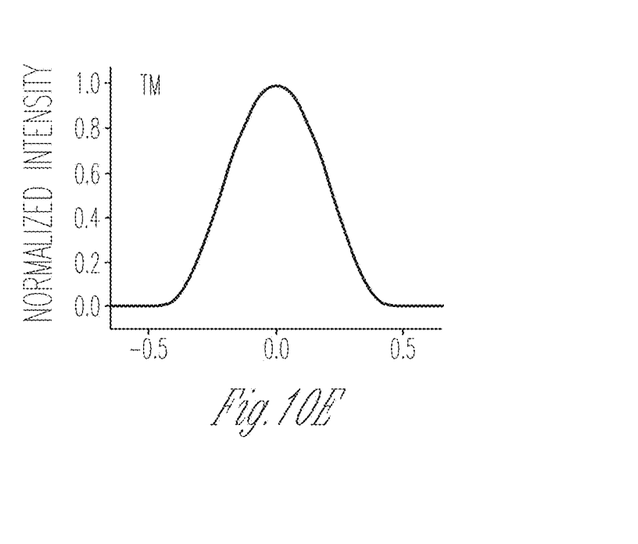

FIG. 10A provides a cross-sectional view of an example strip waveguide as may be used in biosensors in accordance with various embodiments. For purposes of the simulation, the strip waveguide is 800 nm wide and 400 nm tall. FIGS. 10B and 10C show example optical modes in the strip waveguide for transverse electric (TE) and transverse magnetic (TM) polarizations, respectively. As can be seen, for both TE and TM polarized light, an elliptical fundamental mode is obtained at the center of waveguide. FIGS. 10D and 10E are example one-dimensional profiles of the field distribution associated with the optical modes of FIGS. 10B and 10C, respectively, taken along the y-axis. As can be seen, most of the light is contained inside the $Si_3N_4$ strip. Based on quantitative analysis of the simulated modes, the TE polarized waveguide mode has about 3.4% of its intensity in the evanescent wave outside the waveguide. For the TM polarized waveguide mode, the evanescent portion is only 0.2%.

Figure 11A:
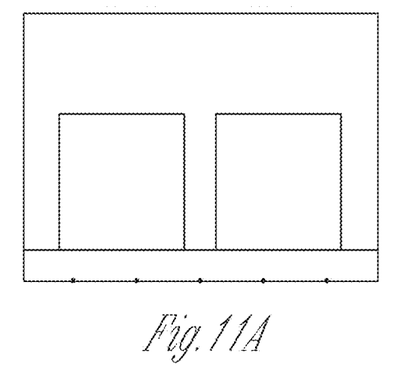
FIG. 11A is a cross-sectional view of a nano-slot waveguide as may be used in biosensors in accordance with various embodiments.
Figure 11B:
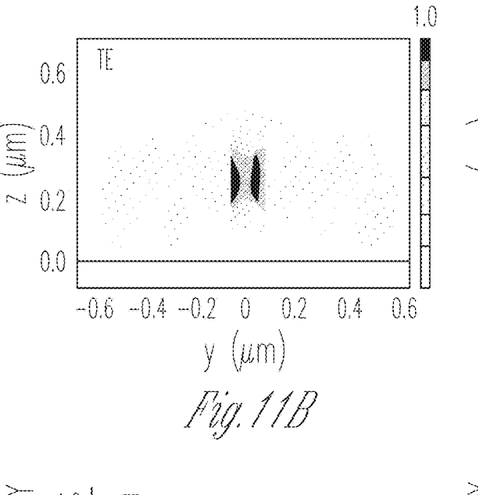
FIGS. 11B and 11C show example optical modes in the nano-slot waveguide of FIG. 11A in two dimensions for transverse electric (TE) and transverse magnetic (TM) polarizations, respectively.
Figure 11C:
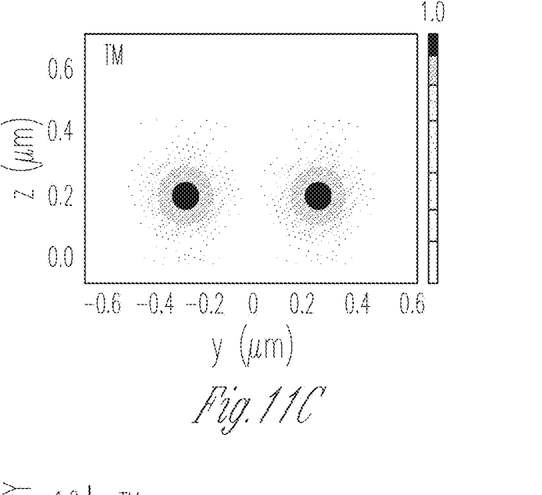
Figure 11D:
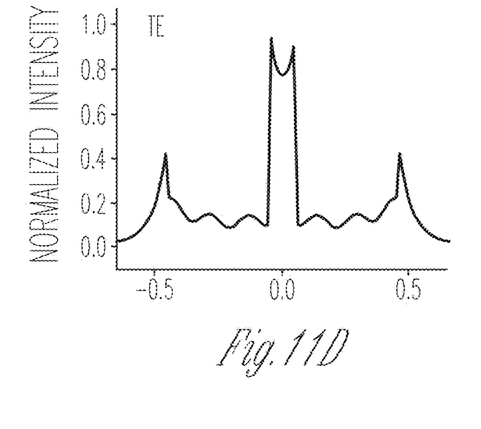
FIGS. 11D and 11E are example one-dimensional profiles of the field distribution associated with the optical modes of FIGS. 11B and 11C, respectively.
Figure 11E:
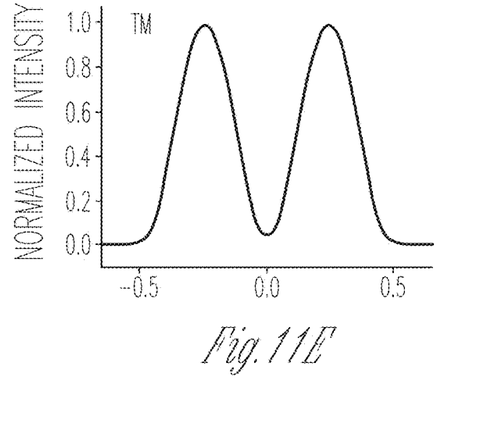

FIG. 11A is a cross-sectional view of a nano-slot waveguide as may be used in biosensors in accordance with various embodiments. As simulated, the nano-slot waveguide is formed of two 400 nm wide waveguide strips separated by a 100 nm space, and is 400 nm tall. FIGS. 11B and 11C show example optical modes in the nano-slot waveguide of FIG. 11A in two dimensions for transverse electric (TE) and transverse magnetic (TM) polarizations, respectively. As can be seen in FIG. 11B, for TE polarization, the field is highly concentrated in the center of the 100 nm nano-slot region, which, in use, can serve as the fluidic channel to be filled with the sample to be analyzed. On the other hand, for TM polarization, as shown in FIG. 11C, only a small portion of the field extends outside the two waveguide strips. FIGS. 11D and 11E are example one-dimensional profiles of the field distribution associated with the optical modes of FIGS. 11B and 11C, respectively. For the TE polarized mode, the nano-slot waveguide has a 50.5% of the light intensity confined in the slot region. By contrast, for the TM polarized mode, the portion of the field extending outside of the waveguide strips is merely 5.9%, which is similar to the TM mode of a single-strip waveguide as shown in FIG. 10A.

Compared to the counterpart single-strip waveguide, the TE mode of the nano-slot waveguide revealed a fourteenfold (14×) enhancement of the optical intensity. This enhanced intensity, in conjunction with the direct overlap between the fluidic channel, where the sample is applied, and the waveguide mode, can significantly improve the overall sensitivity due to the increased light-analyte interaction in the slot region. Beneficially, unlike methods that improve the optical sensitivity by decreasing the waveguide thickness, the nano-slot waveguide converts guided light into a nano-scale optical probe without a reduction in coupling efficiency or increase in the optical loss. Sensitivity enhancement with slot waveguides can be applied to absorption spectroscopy as described herein, but is also applicable to other spectroscopic methods, including fluorescence spectroscopy. For example, the capture agent for the 2019 nCoV N1 marker gene may be labeled with a fluorescent dye such as Cy3, resulting in a DNA sequence 5'-/Cy3/GGT CCA CCA AAC GTA ATG CGG GGT-3'. When the target binds to this sequence, the fluorescence signal changes, as can be detected at the output of the waveguide sensor. This technology is amenable to adaption for many diseases, including recurrent diseases like, e.g., malaria, dengue fever, or measles.

Although embodiments have been described with reference to specific example embodiments, it will be evident that various modifications and changes may be made to these embodiments without departing from the broader scope of the invention. Accordingly, the specification and drawings are to be regarded in an illustrative rather than a restrictive sense.

What is claimed is:

1. A mid-infrared photonic biosensor comprising:
   a substrate;
   an optical waveguide formed on the substrate, the optical waveguide being transparent to light over a range of mid-infrared wavelengths; and
   a biological probe layer disposed on the optical waveguide, the biological probe layer being exposable to a sample and comprising a capture agent that specifically binds to a biological target;

wherein:
the waveguide is configured to pass the light within the range of mid-infrared wavelengths to the biological probe layer; and
a target bound to the biological probe layer is configured to optically interact with an evanescent field of light guided in the waveguide.

2. The photonic biosensor of claim 1, wherein the capture agent comprises at least one of a protein or a polynucleic acid.

3. The photonic biosensor of claim 1, wherein the capture agent captures biological moieties located on the surface of at least one of viruses, bacteria, or fungi.

4. The photonic biosensor of claim 1, wherein the capture agent is specific for a coronavirus.

5. The photonic biosensor of claim 1, wherein the optical waveguide is coated with an adhesion layer, the biological probe layer being disposed on the adhesion layer.

6. The photonic biosensor of claim 1, wherein the adhesion layer comprises a selective silane.

7. The photonic biosensor of claim 1, wherein the substrate comprises an undercladding, the optical waveguide being formed on the undercladding, and wherein the optical waveguide and undercladding are both transparent to light over the range of mid-infrared wavelengths.

8. The photonic biosensor of claim 7, wherein the range of mid-infrared wavelengths extends at least from about 2.5 µm to about 3.8 µm.

9. The photonic biosensor of claim 8, wherein the range of mid-infrared wavelengths extends at least from about 2.5 µm to about 7 µm.

10. The photonic biosensor of claim 1, wherein the optical waveguide is a slot waveguide.

11. A mid-infrared biological sensing system comprising:
a photonic biosensor, the biosensor comprising a waveguide disposed on a substrate, the waveguide being transparent to light over a range of mid-infrared wavelengths, at least a portion of the waveguide having a biological probe layer disposed thereon, the biological probe layer exposable to a sample and comprising a capture agent that specifically binds to a biological target;
a light source configured to couple light within the range of mid-infrared wavelengths into the waveguide at a first end thereof, and
wherein:
the waveguide is configured to pass the light within the range of mid-infrared wavelengths to the biological probe layer; and
a target bound to the biological probe layer is configured to optically interact with an evanescent field of light guided in the waveguide; and
a detector configured to measure the optical interaction between the biological probe layer and the evanescent field of light guided by the waveguide.

12. The sensing system of claim 11, wherein the capture agent comprises at least one of a protein or a polynucleic acid.

13. The sensing system of claim 11, wherein the capture agent captures biological moieties located on the surface of at least one of viruses, bacteria, or fungi.

14. The sensing system of claim 11, wherein the capture agent is specific for a coronavirus.

15. The sensing of claim 11, wherein the at least a portion of the waveguide is coated with an adhesion layer, the biological probe layer being disposed on the adhesion layer.

16. The sensing system of claim 11, wherein the substrate comprises an undercladding, the waveguide being formed on the undercladding, and wherein the waveguide and undercladding are both transparent to light over the range of mid-infrared wavelengths.

17. The sensing system of claim 16, wherein the range of mid-infrared wavelengths extend at least from about 2.5 µm to about 3.8 µm.

18. The sensing system of claim 16, wherein the range of mid-infrared wavelengths extends at least from about 2.5 µm to about 7 µm.

19. The sensing system of claim 11, further comprising:
a computational processing facility configured to process a signal received from the detector to determine spectral properties of the light exiting the waveguide at the second end and measured at the detector and, based on the spectral properties, determine whether the biological target is bound to the biological probe layer.

20. The sensing system of claim 11, further comprising a microfluidic chamber enclosing the photonic biosensor and configured to bring the sample in contact with the biological probe layer.

21. The sensing system of claim 11, wherein at least one of the light source or the detector is monolithically integrated with the photonic biosensor on the substrate.

22. The sensing system of claim 11, wherein the waveguide is a slot waveguide.

23. A biological sensing method comprising:
applying a biological sample to a photonic biosensor, the biosensor comprising a wave guide disposed on a substrate, the waveguide being transparent to light over a range of mid-infrared wavelengths, at least a portion of the waveguide having a biological probe layer, disposed thereon, the biological probe layer comprising a capture agent that specifically binds to a biological target;
cleaning any unbound portion of the biological sample off the photonic biosensor;
coupling light within the range of mid-infrared wavelengths into the waveguide at a first end thereof and measuring light exiting the waveguide at a second end thereof,
passing the light within the range of mid-infrared wavelengths to the biological probe layer;
measuring the optical interaction between the biological probe layer and the evanescent field of light guided by the waveguide; and
computationally processing a signal indicative of the interaction between the biological probe layer and the evanescent field of light guided by the waveguide to determine spectral properties of the light exiting the waveguide at the second end and, based on the spectral properties, determine whether the biological target is bound to the biological probe.

* * * * *